US008759613B1

(12) United States Patent
Davis et al.

(10) Patent No.: US 8,759,613 B1
(45) Date of Patent: Jun. 24, 2014

(54) METHOD OF PRODUCING A LUNASIN POLYPEPTIDE IN PLANTS

(75) Inventors: Keith R. Davis, Owensboro, KY (US); Brian Barnett, Indianapolis, IN (US); Lauren Seber, Owensboro, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 323 days.

(21) Appl. No.: 12/912,381

(22) Filed: Oct. 26, 2010

Related U.S. Application Data

(60) Provisional application No. 61/254,788, filed on Oct. 26, 2009.

(51) Int. Cl.
| | |
|---|---|
| C12N 15/82 | (2006.01) |
| C12N 15/86 | (2006.01) |
| A01H 5/00 | (2006.01) |
| C12N 15/62 | (2006.01) |
| C12P 21/02 | (2006.01) |
| A61K 38/16 | (2006.01) |
| A61P 35/00 | (2006.01) |

(52) U.S. Cl.
USPC ........ 800/288; 800/317.3; 800/280; 435/468; 435/320.1; 435/69.7; 435/91.4

(58) Field of Classification Search
None
See application file for complete search history.

(56) References Cited

U.S. PATENT DOCUMENTS

| | | | |
|---|---|---|---|
| 6,107,287 A * | 8/2000 | de Lumen et al. .......... 514/44 R |
| 6,391,848 B1 | 5/2002 | de Lumen et al. | |
| 6,544,956 B1 | 4/2003 | de Lumen et al. | |
| 7,192,615 B2 | 3/2007 | Liu et al. | |
| 7,309,688 B2 | 12/2007 | Seiberg et al. | |
| 7,375,092 B2 | 5/2008 | de Lumen et al. | |
| 7,404,973 B2 | 7/2008 | Konwinski et al. | |
| 2003/0027765 A1 | 2/2003 | Galvez | |
| 2003/0064121 A1 | 4/2003 | Konwinski et al. | |
| 2003/0224420 A1 | 12/2003 | Hellerstein et al. | |
| 2003/0229038 A1 | 12/2003 | de Lumen et al. | |
| 2007/0054031 A1 | 3/2007 | Liu | |
| 2007/0292494 A1 | 12/2007 | Gieseler et al. | |
| 2008/0003567 A1 | 1/2008 | Rodriguez et al. | |
| 2008/0070827 A1 | 3/2008 | Galvez | |
| 2010/0197594 A1 | 8/2010 | Galvez | |

FOREIGN PATENT DOCUMENTS

| | | | |
|---|---|---|---|
| WO | 0134808 A2 | 5/2001 | |
| WO | WO 0134808 | * 5/2001 | |

OTHER PUBLICATIONS

Carter (Protein purification, Ladisch et al, ACS Symposium Series, American Chemical Society, Chapter 13: Site-Specific proteolysis of fusion proteins, p. 181-193, 1990).*
Li et al (Cancer Gene Therapy, vol. 11, p. 363-370, 2004).*
Wagner et al (Methods, vol. 32, p. 227-234, 2004).*
Scholthof et al (Annu. Rev. Phytopathol, vol. 42, p. 13-34, 2004).*
Peckham et al (Protein Expression and Purification, 49, pp. 183-189, 2006).*
Ampe et al., "The amino-acid sequence of the 2S sulphur-rich proteins from seeds of Brazil nut (*Bertholletia excelsa* H.B.K.)," Eur. J. Biochem., 1986, vol. 159, pp. 597-604.
Chiesa et al., "Reduced mammary tumor progression in a transgenic mouse model fed an isoflavone-poor soy protein concentrate," Mol Nutr Food Res, 2008, vol. 52(10), pp. 1121-1129.
De Lumen, Bo, "Lunasin: a novel cancer preventive seed peptide that modifies chromatin," J AOAC Int, 2008, vol. 91 (4), pp. 932-935.
De Lumen, Bo, "Lunasin: a cancer-preventive soy peptide," Nutr Rev, 2005, vol. 63(1), pp. 16-21.
De Mejia, et al. "Lunasin, with an arginine-glycine-aspartic acid motif, causes apoptosis to L1210 leukemia cells by activation of caspase-3," Mol Nutr Food Res, 2010, vol. 54(3), pp. 406-414.
De Mejia et al., "Lunasin and lunasin-like peptides inhibit inflammation through suppression of NF-kappaB pathway in the macrophage,," Peptides, 2009, vol. 30(12), pp. 2388-2398.
De Mejia et al., "The anticarcinogenic potential of soybean lectin and lunasin," Nutr Rev, 2003, vol. 61(7), pp. 239-246.
Dia et al., "Lunasin promotes apoptosis in human colon cancer cells by mitochondrial pathway activation and induction of nuclear clusterin expression," Cancer Lett, 2010, vol. 295(1), pp. 44-53.
Dia et al., "Presence of lunasin in plasma of men after soy protein consumption," J Agric Food Chem, 2009, vol. 57, pp. 1260-1266.
Dia et al., "Isolation, purification and characterization of lunasin from defatted soybean flour and in vitro evaluation of its anti-inflammatory activity," Food Chemistry, 2009, vol. 114, pp. 108-115.
Dia et al., "Bowman-Birk inhibitor and genistein among soy compounds that synergistically inhibit nitric oxide and prostaglandin E2 pathways in lipopolysaccharide-induced macrophages," J Agric Food Chem, 2008, vol. 56(24), pp. 11707-11717.
Ericson et al., "Structure of the Rapeseed 1.7 S Storage Protein, Napin, and its Precursor," J Biological Chem, 1986, vol. 261, pp. 14576-14581.
Galvez et al., "Chemopreventive property of a soybean peptide (lunasin) that binds to deacetylated histones and inhibits acetylation," Cancer Res, 2001, vol. 61, pp. 7473-7478.
Galvez et al., "A soybean cDNA encoding a chromatin-binding peptide inhibits mitosis of mammalian cells," Nat Biotechnol, 1999, vol. 17, pp. 495-500.
Gonzalez et al., "Lunasin concentration in different soybean genotypes, commercial soy protein, and isoflavone products," J Agric Food Chem, 2004, vol. 52, pp. 5882-5887.
Hernandez-Ledesma et al., "Lunasin, a novel seed peptide for cancer prevention," Peptides, 2009, vol. 30(2), pp. 426-430.
Hsieh et al., "Lunasin, a novel seed peptide, sensitizes human breast cancer MDA-MB-231 cells to aspirin-arrested cell cycle and induced apoptosis," Chem Biol Interact, 2010a, vol. 186(2), pp. 127-134.
Hsieh et al., "Complementary roles in cancer prevention: protease inhibitor makes the cancer preventive peptide lunasin bioavailable," PLoS One, 2010b, vol. 5(1), pp. e8890.

(Continued)

*Primary Examiner* — Cathy Kingdon Worley
*Assistant Examiner* — Stephen Uyeno
(74) *Attorney, Agent, or Firm* — Stites & Harbison PLLC; Mandy Wilson Decker

(57) ABSTRACT

A method of producing a lunasin polypeptide in a plant includes expressing a fusion protein including the lunasin polypeptide in the plant and cleaving the lunasin polypeptide from the fusion protein.

15 Claims, 3 Drawing Sheets

(56) References Cited

OTHER PUBLICATIONS

Hsieh et al., "Dynamics of keratinocytes in vivo using HO labeling: a sensitive marker of epidermal proliferation state," J Invest Dermatol, 2004. vol. 123(3), pp. 530-536.

Jeong et al., "The cancer preventive seed peptide lunasin from rye is bioavailable and bioactive," Nutr Cancer, 2009, vol. 61(5), pp. 680-686.

Jeong et al., "Cancer-preventive peptide lunasin from *Solanum nigrum* L. inhibits acetylation of core histones H3 and H4 and phosphorylation of retinoblastoma protein (Rb)," J Agric Food Chem, 2007c, vol. 55(26), pp. 10707-10713.

Jeong et al., "The cancer preventive peptide lunasin from wheat inhibits core histone acetylation," Cancer Lett, 2007b, vol. 255, pp. 42-48.

Jeong et al., "Inhibition of core histone acetylation by the cancer preventive peptide lunasin," J Agric Food Chem, 2007a, vol. 55, pp. 632-637.

Jeong et al., "Characterization of lunasin isolated from soybean," J Agric Food Chem, 2003, vol. 51, pp. 7901-7906.

Jeong et al., "Barley lunasin suppresses ras-induced colony formation and inhibits core histone acetylation in mammalian cells," J Agric Food Chem, 2002, vol. 50, pp. 5903-5908.

Krebbers et al., "Determination of the Processing Sites of an *Arabidopisis* 2S Albumin and Characterization of the Complete Gene Family," Plant Physiol, 1988, vol. 81, pp. 859-866.

Lam et al., "Lunasin suppresses E1A-mediated transformation of mammalian cells but does not inhibit growth of immortalized and established cancer cell lines," Nutr Cancer, 2003, vol. 47(1), pp. 88-94.

Li et al, "Synthesis and characterization of a high-affinitiy αvβ6-specific ligand for in vitro and in vivo applications," Mol. Cancer. Ther., 2009, vol. 8(5), pp. 1239-1248.

Lin et al., "The expression and processing of two recombinant 2S albumins from soybean (Glycine max) in the yeast *Pichia pastoris*," Biochimica et Biophysica Acta, 2004, vol. 1698, pp. 203-212.

Liu et al., "Recombinant expression of bioactive peptide lunasin in *Escherichia coli*," Appl Microbiol Biotechnol, 2010, vol. 88, pp. 177-186.

Maldonado-Cervantes et al., "Amaranth lunasin-like peptide internalizes into the cell nucleus and inhibits chemical carcinogen-induced transformation of NIH-3T3 cells," Peptides, 2010, doi:10.1016/j.peptides2010.06.014.

Martin et al., High-yield, in vitro protein expression using a continuous-exchange, coupled transcription/ translation system, Biotechniques, 2001, vol. 31(4), pp. 948-953.

Odani et al., "Amino Acid Sequence of a Soybean (Glycine max) Seed Polypeptide Having a Poly(L-Aspartic Acid) Structure," The Journal of Biological Chemistry, 1987, vol. 262, pp. 10502-10505.

Park et al., "In vitro digestibility of the cancer-preventive soy peptides lunasin and BBI," J Agric Food Chem, 2007, vol. 55, pp. 10703-10706.

Park et al., "Contents and bioactivities of lunasin, bowman-birk inhibitor, and isoflavones in soybean seed," J Agric Food Chem, 2005, vol. 53, pp. 7686-7690.

Silva-Sanchez et al., "Bioactive peptides in amaranth (*Amaranthus hypochondriacus*) seed," J Agric Food Chem, 2008, vol. 56(4), pp. 1233-1240.

Wang et al., "Analysis of soybean protein-derived peptides and the effect of cultivar, environmental conditions, and processing on lunasin concentration in soybean and soy products," J AOAC Int, 2008b, vol. 91, pp. 936-946.

Wang et al., "beta-Conglycinins among sources of bioactives in hydrolysates of different soybean varieties that inhibit leukemia cells in vitro," J Agric Food Chem, 2008a, vol. 56, pp. 4012-4020.

\* cited by examiner

**SEQ ID NO: 1 - Lunasin (*Glycine max*)**
M-S-K-W-Q-H-Q-Q-D-S-C-R-K-Q-L-Q-G-V-N-L-T-P-C-E-K-H-I-M-E-K-I-Q-
G-R-G-D-D-D-D-D-D-D-D Met-Ser-Lys-Trp-Gln-His-Gln-Gln-Asp-Ser-Cys-Arg-Lys-Gln-Leu-Gln-
Gly-Val-Asn-Leu-Thr-Pro-Cys-Glu-Lys-His-Ile-Met-Glu-Lys-Ile-Gln-
Gly-Arg-Gly-Asp-Asp-Asp-Asp-Asp-Asp-Asp-Asp

SEQ ID NO: 2 - Fusion Protein: RGD-Lunasin
M-R-G-D-L-A-T-L-R-Q-L-S-K-W-Q-H-Q-Q-D-S-C-R-K-Q-L-Q-G-V-N-L-T-P-
C-E-K-H-I-M-E-K-I-Q-G-R-G-D-D-D-D-D-D-D-D Met-Arg-Gly-Asp-Leu-Ala-Thr-Leu-Arg-Gln-Leu-Ser-Lys-Trp-Gln-His-
Gln-Gln-Asp-Ser-Cys-Arg-Lys-Gln-Leu-Gln-Gly-Val-Asn-Leu-Thr-Pro-
Cys-Glu-Lys-His-Ile-Met-Glu-Lys-Ile-Gln-Gly-Arg-Gly-Asp-Asp-Asp-
Asp-Asp-Asp-Asp-Asp-Asp

SEQ ID NO: 3 - Fusion Protein: Linker RGD Lunasin
GFP-----G-G-G-S-G-G-G-S-G-G-G-S-L-V-P-R-G-S-R-G-D-L-A-T-L-R-Q-L-
S-K-W-Q-H-Q-Q-D-S-C-R-K-Q-L-Q-G-V-N-L-T-P-C-E-K-H-I-M-E-K-I-Q-G-
R-G-D-D-D-D-D-D-D-D Gly-Gly-Gly-Ser-Gly-Gly-Gly-Ser-Gly-Gly-Gly-Ser-Leu-Val-Pro-Arg-
Gly-Ser-Arg-Gly-Asp-Leu-Ala-Thr-Leu-Arg-Gln-Leu-Ser-Lys-Trp-Gln-
His-Gln-Gln-Asp-Ser-Cys-Arg-Lys-Gln-Leu-Gln-Gly-Val-Asn-Leu-Thr-
Pro-Cys-Glu-Lys-His-Ile-Met-Glu-Lys-Ile-Gln-Gly-Arg-Gly-Asp-Asp-
Asp-Asp-Asp-Asp-Asp-Asp-Asp

SEQ ID NO: 4 - Fusion Protein: GFP-Linker-Lunasin
GFP-----G-G-G-S-G-G-G-S-G-G-G-S-L-V-P-R-G-S-K-W-Q-H-Q-Q-D-S-C-R-
K-Q-L-Q-G-V-N-L-T-P-C-E-K-H-I-M-E-K-I-Q-G-R-G-D-D-D-D-D-D-D-D Gly-Gly-Gly-Ser-Gly-Gly-Gly-Ser-Gly-Gly-Gly-Ser-Leu-Val-Pro-Arg-
Gly-Ser-Lys-Trp-Gln-His-Gln-Gln-Asp-Ser-Cys-Arg-Lys-Gln-Leu-Gln-
Gly-Val-Asn-Leu-Thr-Pro-Cys-Glu-Lys-His-Ile-Met-Glu-Lys-Ile-Gln-
Gly-Arg-Gly-Asp-Asp-Asp-Asp-Asp-Asp-Asp-Asp The solid underline identifies the published lunasin peptide sequence, the
dashed underline identifies the region representing the targeting signal
"RGD" used to direct lunasin to cancer cells expressing αvβ6 integrin, and
the dotted underline indentifies the linker sequence containing a thrombin
cleavage site that is used to create protein fusion constructs.

METHOD OF PRODUCING A LUNASIN POLYPEPTIDE IN PLANTS

GOVERNMENT INTEREST

This invention was made with government support under grant number W81XWH-09-2-0022 awarded by the United States Army. The government has certain rights in the invention.

RELATED APPLICATIONS

This application claims priority from U.S. Provisional Application Ser. No. 61/254,788 filed Oct. 26, 2009, the entire disclosure of which is incorporated herein by this reference.

TECHNICAL FIELD

The presently-disclosed subject matter relates to a method of producing a lunasin polypeptide. In particular, the presently-disclosed subject matter relates to a method of producing a lunasin polypeptide using a plant-based expression system.

INTRODUCTION

Wild type lunasin from soybean is a polypeptide having 43-44 amino acids with a C-terminal end of nine consecutive aspartic acid residues (SEQ ID NO: 1) derived from post-translational processing of a 2S albumin protein encoded by the Gm2S gene. Lunasin was originally isolated from soybean but has been reported to have been found in a variety of plant species at relatively low levels. Initial studies demonstrated that lunasin was toxic to both prokaryotic and eukaryotic cells when expressed intracellularly. This toxicity has been attributed to the ability of lunasin to bind to chromatin and specific structures required for mitosis. Later studies demonstrated that lunasin can prevent the transformation of mammalian cells by chemical carcinogens or viral oncogenes, however, the initial published studies indicate that lunasin has little effect on normal or established cancer cell lines. Recent studies have shown that lunasin does inhibit the proliferation of specific cancer cell lines. This chemopreventive effect on cells undergoing a transformation event is thought to be mediated by the binding of lunasin to deacetylated core histones and/or exerting its effects via an epigenetic mechanism that disrupts the normal dynamics of histone acetylation-deacetylation.

Although the potential cancer-chemopreventive activity of lunasin has been known for almost a decade, little progress has been made to demonstrate clinical relevance because of limitations on the ability to produce large enough quantities of lunasin at an effective cost to conduct large-scale animal studies and human clinical trials.

Initial attempts to express lunasin in *E. coli*, and animal cells have been unsuccessful, thus limiting studies to quantities of lunasin that can be synthesized or purified from natural sources. All published research literature available at the time the present application was filed indicates that lunasin is toxic when expressed in cells and there are no peer-reviewed or substantiated accounts of lunasin being successfully expressed in any form in a eukaryotic expression system. It was indicated in a patent application that lunasin had been expressed in yeast (WO 01/034804), however the data presented do not provide any indication to the amounts of lunasin that can be produced, nor has this research ever appeared in any other publication. Indeed, it has been published that lunasin has been produced for studies using in vitro translation, because it cannot be expressed in whole cells. See e.g., Martin, et al. (2001). Biotechniques 31, 948.

Accordingly, there remains a need in the art for a cost-effective method of producing lunasin on a larger scale than via currently-available techniques, in a cost-effective manner.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a method of producing a lunasin polypeptide in a plant, including expressing a fusion protein comprising the lunasin polypeptide in the plant.

In some embodiments, the method includes providing an expression vector comprising a polynucleotide encoding a fusion protein including the lunasin polypeptide, a second polypeptide, and a site-specific protease cleavage site; transcribing the polynucleotide; introducing the transcribed polynucleotide into a plant cell; expressing the fusion protein from the transcribed polynucleotide within the plant cell; isolating the fusion protein; and using a protease of the site-specific protease cleavage site to obtain the lunasin polypeptide or a desired lunasin polypeptide-containing fusion protein.

In some embodiments, the method of producing a lunasin polypeptide in a plant, includes providing an expression vector comprising a polynucleotide encoding the fusion protein; transcribing the polynucleotide; introducing the transcribed polynucleotide into a plant cell; and expressing the fusion protein from the transcribed polynucleotide within the plant cell.

In some embodiments, the expression vector is a transient expression vector, and the plant cell is a non-dividing plant cell. In some embodiments, the expression vector is a tobacco mosaic virus (TMV)-based DNA plasmid.

In some embodiments, introducing the transcribed polynucleotide into a plant cell comprises infecting the plant cell with the transcribed polynucleotide. In some embodiments, the plant cell is a *Nicotiana benthamiana* cell.

In some embodiments, the fusion protein further comprises a second polypeptide and a site-specific protease cleavage site. In some embodiments, the second polypeptide is green fluorescent protein. In some embodiments, the second polypeptide is a targeting signal for directing the lunasin to a target cell.

In some embodiments, the method includes isolating the fusion protein comprising the lunasin polypeptide and the targeting signal for directing the lunasin polypeptide to a target cell.

In some embodiments, the method includes isolating the fusion protein. In some embodiments, the method includes cleaving the lunasin polypeptide from the fusion protein. In some embodiments, the lunasin polypeptide is a lunasin polypeptide-containing fusion protein, i.e., the desired product being isolated is a lunasin polypeptide, further comprising additional amino acids. In some embodiments, the lunasin polypeptide-containing fusion protein includes a polypeptide targeting signal for directing the lunasin polypeptide to a target cell.

In some embodiments, the lunasin polypeptide is produced in amounts of about >100 mg/kg fresh weight plant tissue.

The presently-disclosed subject matter includes a composition useful for treating cancer, including a lunasin polypeptide and a polypeptide targeting signal for directing the lunasin polypeptide to a target cell. In some embodiments, the lunasin polypeptide and the polypeptide targeting signal are provided as a fusion protein.

The presently-disclosed subject matter includes a method for treating cancer, including administering a composition as described herein to a subject in need thereof.

The presently-disclosed subject matter includes a method for treating inflammation-related diseases, including administering a composition as described herein to a subject in need thereof.

The presently-disclosed subject matter includes a kit for producing a lunasin polypeptide in a plant, including an expression vector comprising a polynucleotide encoding a fusion protein including the lunasin polypeptide, second polypeptide, and a site-specific protease cleavage site. In some embodiments, the kit includes a protease of the site-specific protease cleavage site.

BRIEF DESCRIPTION OF THE DRAWINGS

FIG. 4 includes amino acid sequences referenced herein.

BRIEF DESCRIPTION OF THE SEQUENCE LISTING

Figure 1:
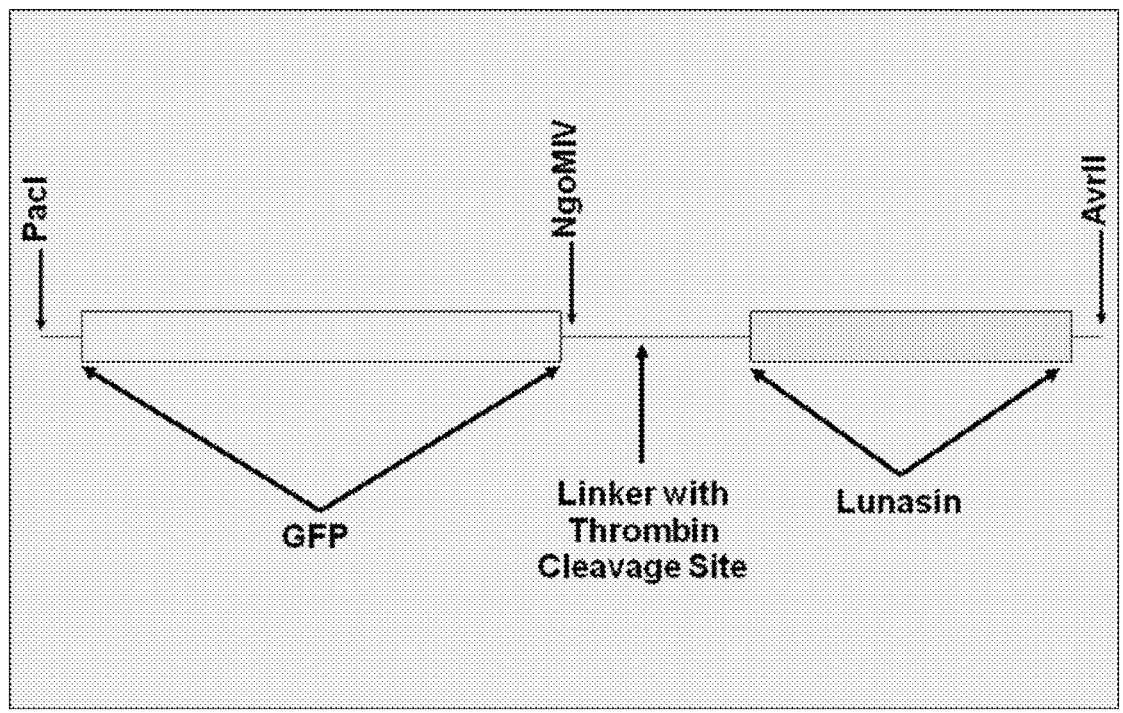
FIG. 1 is schematic representation of a lunasin expression strategy that allows lunasin and modified forms of lunasin to be expressed as part of a green fluorescent protein (GFP) fusion protein.

SEQ ID NO: 1 is an amino acid sequence of the wild type lunasin polypeptide from *Glycine max* (soybean).

SEQ ID NO: 2 is an amino acid sequence of a fusion protein including an RGD targeting signal and a lunasin polypeptide.

SEQ ID NO: 3 is an amino acid sequence of a fusion protein including a linker, an RGD targeting signal, and a lunasin polypeptide, which can be used to create a fusion protein including GFP.

SEQ ID NO: 4 is an amino acid sequence of a fusion protein including a linker and a lunasin polypeptide, which can be used to create a fusion protein including GFP.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes lunasin polypeptides, lunasin polypeptide fusion proteins, compositions including lunasin polypeptides, and methods for making and using the polypeptides and compositions.

The presently-disclosed subject matter includes methods of producing a lunasin polypeptide in a plant. Without wishing to be bound by theory or mechanism, it is believed that previous attempts to express lunasin in a cell were not possible due to the ability of lunasin to inhibit mitosis and/or interfere with chromatin modifications required for normal cell function. (Galvez and de Lumen, 1999; de Lumen, 2008; Hernandez-Ledesma et al., 2009). In this regard, the expressed lunasin becomes toxic to the host cell, and the express system becomes inoperable. Indeed, the present inventors demonstrated that an expression attempt of wild type lunasin in *Nicotiana benthamiana* was unsuccessful (data not shown). Specifically, the *N. benthamiana* plants became necrotic and failed to express detectable amounts of lunasin when attempts were made to express wild type lunasin in the plants. However, the present inventors have surprisingly found that lunasin can be successfully expressed as a fusion protein. Previous attempts to express a lunasin-containing fusion protein in mammalian cells resulted in toxicity and cell death.

Accordingly, the presently-disclosed subject matter includes a method of producing a lunasin polypeptide in a plant, including expressing a fusion protein comprising the lunasin polypeptide in the plant.

As used herein, the term "lunasin polypeptide" is inclusive of wild type lunasin, including wild type lunasin from soybean (SEQ ID NO: 1) and other plants, as well as functional variants and functional fragments thereof.

As used herein, the term "fusion protein" refers to a protein including more than one identifiable polypeptide. For example, a lunasin polypeptide-containing fusion protein includes a lunacin polypeptide and additional amino acids. In some embodiments, the number of additional amino acids is sufficient to allow the fusion protein including the lunasin polypeptide to be expressed in the cell, without the resulting in the expressed fusion protein becoming toxic to the host cell (e.g., without the plants becoming necrotic).

The term "fragment", when used in reference to a lunasin polypeptide, refers to a polypeptide in which amino acid residues are deleted as compared to the reference polypeptide, wild type lunasin, but where the remaining amino acid sequence is usually identical to the corresponding positions in the reference polypeptide. Such deletions can occur at the amino-terminus or carboxy-terminus of the reference polypeptide, or alternatively both. In some cases, such deletions can occur within the reference polypeptide. Fragments typically are at least 17, 18, 19, 20, 21, 22, 23, 24, 25, 26, 27, 28, 29, 30, 31, 32, 33, 34, 35, 36, 37, 38, 39, 40, 41, or 42 amino acids long.

A fragment can also be a "functional fragment," in which case the fragment retains some or all of the desired activity of the reference polypeptide, or has enhanced activity relative to the reference polypeptide. For example, in some embodiments, a functional fragment of wild type lunasin can retain some or all of the chemotherapeutic activity of the reference polypeptide.

The term "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide or additional amino acids have been added to either the N-terminal or C-terminal ends of the reference polypeptide. A variant can also be a "functional variant," in which the variant retains some or all of the activity of the reference protein, or has enhanced activity relative to the reference polypeptide. For example, a functional variant of a wild type lunasin can retain some or all of the chemotherapeutic activity of the reference polypeptide. The term functional variant does not include variants that lose all biological activity or other desired activity of wild-type lunasin.

The term functional variant includes a functional variant of a functional fragment of a reference polypeptide. The term functional variant further includes conservatively substituted variants. The term "conservatively substituted variant" refers to a peptide comprising an amino acid residue sequence that differs from a reference peptide by one or more conservative amino acid substitution, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein.

In some embodiments of the presently-disclosed subject matter, the plant-produced fusion protein can include a site-specific protease cleavage site to allow the expressed lunasin polypeptide (or a desired lunasin polypeptide-containing fusion protein) to be released (e.g., cleaved) from the expressed fusion protein and purified.

In some embodiments, the method of producing a lunasin polypeptide in a plant includes: providing an expression vector comprising a polynucleotide encoding a fusion protein including the lunasin polypeptide; transcribing the polynucleotide; introducing the transcribed polynucleotide into a plant cell; expressing the fusion protein from the transcribed polynucleotide within the plant cell, and isolating and obtaining the lunasin polypeptide. In some embodiments, the polynucleotide encoding the lunasin polypeptide encodes an amino acid sequence comprising the sequence of SEQ ID NO: 1. In some embodiments, the lunasin polypeptide comprises the amino acid sequence of SEQ ID NO: 1. In some embodiments, the lunasin polypeptide comprises a functional fragment or functional variant of the amino acid sequence of SEQ ID NO: 1. In some embodiments, the lunasin polypeptide is expressed as a fusion protein. In some embodiments, the fusion protein comprises the lunasin polypeptide, and a second polypeptide, wherein the fusion protein includes a site-specific protease cleavage site.

In some embodiments, the method of producing a lunasin polypeptide in a plant includes: providing an expression vector comprising a polynucleotide encoding a fusion protein including the lunasin polypeptide, a second polypeptide, and a site-specific protease cleavage site; transcribing the polynucleotide; introducing the transcribed polynucleotide into a plant cell; expressing the fusion protein from the transcribed polynucleotide within the plant cell; isolating the fusion protein; cleaving the second polypeptide from the lunasin polypeptide using a protease of the site-specific protease cleavage site; and obtaining the lunasin polypeptide.

With regard to the expression vector, in some embodiments the expression vector is a tobacco mosaic virus (TMV)-based DNA plasmid. In some embodiments, the polynucleotide encoding the fusion protein encodes an amino acid sequence comprising the sequence of SEQ ID NO: 2, 3, or 4. In some embodiments, the fusion protein comprises the amino acid sequence of SEQ ID NO: 2, 3, or 4.

Without wishing to be bound by theory or mechanism, because wild-type lunasin can be toxic to a dividing cell it is believed that some lunasin polypeptides can be more readily expressed using a transient expression system in plants, where the cell or cells that express the protein in a plant are not dividing cells. In this regard, in some embodiments, a transient expression system is employed; however, in other embodiments, depending in part on the particular lunasin polypeptide desired to be expressed, it can be possible to use a transgenic plant.

With regard to the step of transcribing the polynucleotide in plants, in some embodiments, the polynucleotide is under the control of a regulatory element. In some embodiments, the regulatory element can be a promoter, e.g., a viral promoter, or any promoter that can support expression in a plant cell. In some embodiments, the transcription of viral vector containing lunasin-encoding sequences includes in vitro transcription using T7 polymerase.

With regard to the step of introducing the transcribed polynucleotide into a plant cell, in some embodiments, the lunasin-encoding polynucleotide sequence is introduced by infecting the plant cell with the in vitro transcribed polynucleotides, which can be an infectious RNA polynucleotide. Alternatively, the lunasin-encoding sequence is introduced into plants using infectious virus particles where the viral genome has been modified to include lunasin-encoding sequences, e.g. Tobacco Mosaic Virus (TMV). In some embodiments, the plant cell is a *Nicotiana benthamiana* cell. In some embodiments, the plant cell is a plurality of *Nicotiana benthamiana* cells. In some embodiments, the plurality of *Nicotiana benthamiana* cells is a *Nicotiana benthamiana* plant. Various other plant cells could be used with appropriate expression systems selected based on the desired plant cell, as will be understood by those skilled in the art.

With regard to the step of isolating the fusion protein, in some embodiments, the isolation includes extracting the plant cell, or plurality of plant cells, in water or a buffer such as PBS. The resulting extract can then be clarified by passage through cheesecloth or Miracloth, or by centrifugation. The clarified extract can be subjected to ultrafiltration (e.g., 30 kD molecular-weight cutoff membrane) and the lunasin fusion-enriched permeate collected. The permeate can be subjected to ion-exchange chromatography (e.g., quaternary amino (Q) column) to obtain partially purified lunasin fusion. The Q-column purified lunasin fusion can then be subjected to size exclusion chromatography or other protein chromatography methods know to those skilled in the art, to obtain highly purified lunasin fusion protein. The purified lunasin fusion protein is treated with thrombin to release lunasin (or a modified form of lunasin) and the thrombin inactivated by heat treatment. The lunasin product can be purified using size exclusion and/or ion-exchange chromatography. As will be understood by those of ordinary skill in the art, the various steps take to affect isolation of the fusion protein can vary even for the same fusion protein, but can be optimized. The steps taken to optimize a particular isolation could depend on the specific characteristics of the fusion protein, e.g., the non-lunasin polypeptide component, as will be understood by those of ordinary skill in the art.

When the fusion protein has been purified, if desired, the lunasin polypeptide can be released using a protease acting upon the site-specific protease cleavage site. As will be apparent to those skilled in the art upon studying this application, a desired fusion protein containing the lunasin polypeptide can be released for a larger purified fusion protein using a protease acting upon the site-specific protease cleavage site. In this manner the desired lunasin polypeptide or the desired fusion protein containing the lunasin polypeptide can be obtained.

In some embodiments, the method allows for the lunasin polypeptide to be produced in amounts of about 100-500 mg/kg fresh weight plant tissue.

The presently-disclosed subject matter further includes a kit for producing a lunasin polypeptide in a plant. In some embodiments, the kit includes: an expression vector comprising a polynucleotide encoding a fusion protein including the lunasin polypeptide; a second polypeptide; and a site-specific protease cleavage site. The kit can further include a protease of the site-specific protease cleavage site for cleaving the second polypeptide from the lunasin polypeptide. The kit can further include instructions for expressing, isolating, and obtaining the lunasin polypeptide.

In some embodiments of the presently disclosed subject matter, fusion proteins are provided that include a lunasin polypeptide and a second polypeptide. In some embodiments, the second polypeptide is fused to the C-terminal end of the lunasin polypeptide. In some embodiments, the second polypeptide is fused to the N-terminal end of the lunasin polypeptide such that the poly-Asp tail of the lunasin polypeptide is exposed. The second polypeptide can be selected for its desired characteristics, for example, it can be desirable for certain research tools to use a second polypeptide that is capable of visualization, such as green fluorescent protein (GFP). A fusion protein including GFP can be used, for example, to monitor the protein within a cell. For another example, a second polypeptide can be selected for characteristics that provide the fusion protein with enhanced potential as a therapeutic agent. In this regard, in some embodiments, the second polypeptide includes a targeting signal to direct the lunasin polypeptide to a specific cancer cell for interaction therewith. In some embodiments, the targeting signal can be an integrin targeting signal, such as the "RGD" integrin targeting signal (dashed underline in SEQ ID NO: 2 of FIG. 4) (Li, et al. (2009) Mol Cancer Ther). Other examples of targeting signals that can be used include, but are not limited to: cytokines, chemokines, TGF-β, Activins, Nodals, BMP Ligans (such as BMP-2, BMP-4, and MIS), Wnt signaling ligands, a hormone receptor that binds protein hormones (such as EGF Receptor), a protein/receptor that binds a peptide ligand that is overexpressed in a cancer cell (such as Tie2 receptor).

In some embodiments, the fusion protein of the presently-disclosed subject matter can include a site-specific protease cleavage site. In some embodiments, the fusion protein can include a linker. In some embodiments the fusion protein can include a linker including a site-specific protease cleavage site. As noted herein, the site-specific protease cleavage site can be useful for releasing a portion (e.g., a second fusion protein portion, or the lunasin polypeptide portion) of the fusion protein that is desired for isolation. In some embodiments, the site-specific protease cleavage site can be a thrombin cleavage site.

In some embodiments, a fusion protein including a lunasin polypeptide, green fluorescent protein (GFP), and a linker that includes a site-specific protease cleavage site (e.g., thrombin) can be expressed, purified, and the lunasin polypeptide can be isolated for use. The isolated lunasin polypeptide can be used for treating a cancer or inflammation-related diseases. In some embodiments, the fusion protein can include the amino acid sequence of SEQ ID NO: 4.

In some embodiments, a fusion protein can be expressed including a lunasin polypeptide and a targeting signal, e.g., RGD. In some embodiments, the fusion protein can include the amino acid sequence of SEQ ID NO: 2. The targeting signal of the fusion protein can direct the lunasin polypeptide to specific cancer cells for interaction therewith. In some embodiments, a fusion protein can be expressed including a lunasin polypeptide, a second polypeptide, and a third polypeptide. In some embodiments, the second polypeptide can include a targeting signal, and the third polypeptide can comprise GFP. In some embodiments, the fusion protein can also include a linker. In some embodiments, the fusion protein can include a site-specific protease cleavage site that allows a second fusion protein comprising the lunasin polypeptide and the polypeptide including a targeting signal to be released from the third polypeptide. In some embodiments, the fusion protein can include the amino acid sequence of SEQ ID NO: 3.

The presently-disclosed subject matter includes a composition that comprises a lunasin polypeptide. In some embodiments, the lunasin polypeptide is comprised within a fusion protein, as noted above. In some embodiments, a composition including lunasin and a targeting signal can be provided, e.g., a fusion protein including lunasin and a polypeptide targeting signal that directs the lunasin to specific cancer cells for interaction therewith. The targeted composition allows for increased bioavailability, activity, and efficacy, and promotes stability in vivo.

In some embodiments, the composition includes a lunasin polypeptide and a polypeptide targeting signal for directing the lunasin to a target cell. In some embodiments, the lunasin polypeptide and the polypeptide targeting signal are provided as a fusion protein. In some embodiments, the fusion protein comprises the amino acid sequence of SEQ ID NO: 2, 3, or 4.

As will be understood by those skilled in the art, formulations of composition containing the lunasin polypeptide can be provided for various types of delivery, e.g., oral, nasal, topical, injectable, etc. Delivery to mucosal sites, e.g., nasal delivery formulation, has benefits such as increased uptake, and decreased amount of lunasin required for efficacy, because it bypasses digestion, where as much as 95% of orally-administered lunasin can be degraded. The lunasin polypeptide can be formulated as a topical gel/lotion to prevent skin cancer. The lunasin polypeptide can be used as an injectable agent. In some embodiments, the injectable agent can be used as a prophylactic agent in individuals acutely exposed to chemical carcinogens or radiation. It can also be useful as an adjuvant treatment for children undergoing chemo- or radiation-treatment for cancers when there is a concern that the treatments may be mutagenic/carcinogenic.

The presently-disclosed subject matter further includes a method for treating cancer using a lunasin polypeptide as described herein. In some embodiments, the method includes administering the composition comprising the lunasin polypeptide, as described herein, to a subject in need thereof.

As used herein, the term "subject" refers to human and other animal subjects. Thus, veterinary therapeutic uses are provided in accordance with the presently disclosed subject matter. For example, a prophylactic treatment is contemplated for animals that have a genetic susceptibility to developing specific cancers. As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter is further illustrated by the following specific but non-limiting examples. The following examples may include compilations of data that are representative of data gathered at various times during the course of development and experimentation related to the present invention.

EXAMPLES

Lunasin is a small peptide consisting of 43-44 amino acids with a C-terminal end containing nine consecutive aspartic acid residues. Initial studies concerning the peptide's chemopreventive activity indicated lunasin kills cancer cells by disrupting mitosis and causing apoptosis. Lunasin was originally derived from soybeans but has been found in a variety of plant species at relatively low levels. Attempts to express the lunasin peptide in yeast and animal cells have not been successful. Therefore, the present inventors have developed a transient, plant-based expression system utilizing the Tobacco Mosaic Virus vector, Geneware®, and tobacco for large-scale production of lunasin. This system will allow production of purified lunasin in larger quantities.

A transient, tobacco-based (*Nicotiana benthamiana*) expression system based on the Tobacco Mosaic Virus vector, Geneware®, was used to study large-scale production of lunasin. With reference to FIG. 1, FIGS. 2A and 2B, and FIGS. 3A and 3B the present inventors successfully expressed lunasin and a modified form of lunasin in *Nicotiana benthamiana* plants as a Green Fluorescent Protein (GFP) fusion at levels approaching 100 mg/kg fresh weight tissue.

The strategy for expressing lunasin and modified forms of lunasin as part of a fusion protein with GFP will be described with reference to FIG. 1. A Geneware® vector was constructed that contained a GFP-encoding sequence that contains an NgoMV restriction site at the C-terminal end of GFP. A synthetic gene with a 5' NgoMV restriction site, a linker sequence (dotted underline of SEQ ID NOS: 3 and 4, as shown in FIG. 4), followed by the desired lunasin sequence and a 3' AvrII restriction site. The synthetic gene sequence is cloned into the Geneware® vector as an NgoMIV-AvrII fragment, resulting in a translational fusion with GFP.

Figure 2:
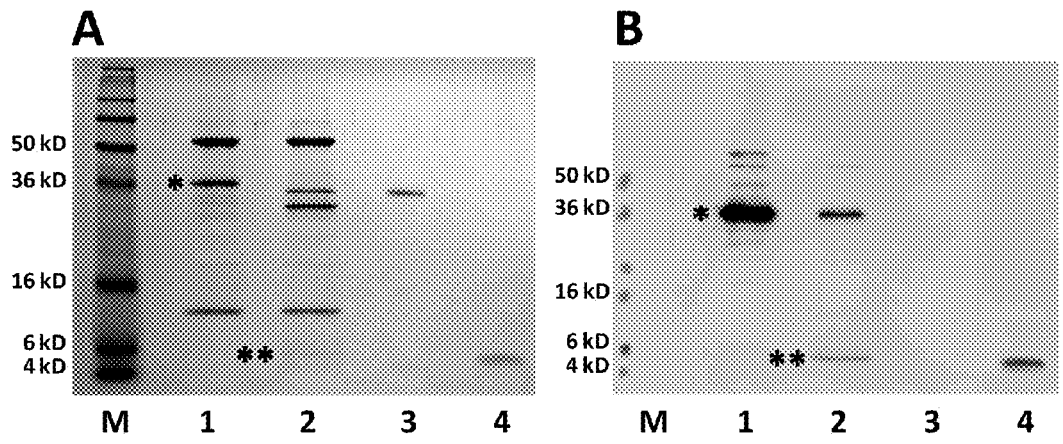
FIG. 2A is a Commassie-stained gel showing that the GFP-lunasin fusion protein was expressed in *Nicotiana benthamiana* plants and that lunasin can be released from the fusion protein by protease cleaveage.
FIG. 2B is a corresponding immunoblot probed with an antibody against lunasin confirming that the GFP-lunasin fusion protein was expressed in *Nicotiana benthamiana* plants and that lunasin can be released from the fusion protein by protease cleaveage.

With reference to FIG. 2, lunasin was successfully expressed in a fusion protein, and released from the fusion protein. FIG. 2 includes an analysis of partially purified GFP-lunasin fusion protein expressed in tobacco plants and the successful release of lunasin from the fusion protein by thrombin cleavage. An expression construct was generated using a Geneware® vector such that native lunasin is translationally fused to the C-terminal end of GFP using a peptide linker containing a cleavage site for the protease, thrombin (See SEQ ID NO: 4). Infectious transcripts were generated from the Geneware® construct and inoculated into *Nicotiana benthamiana* plants. Infected plants were harvested 5-10 days after inoculation and tissues extracted with phosphate buffered saline (58.5 mM Na2HPO4, 17 mM NaH2PO$_4$, 68.4 mM NaCl, 20 mM ascorbic acid, 10 mM sodium metabisulfite). Crude extracts were filtered through 4 layers of cheesecloth and 1 layer of miracloth. The filtrate was then centrifuged at 10,000×G for 10 minutes to generate a clarified extract. The clarified extract was subjected to anion-exchange chromatography on a Q Sepharose FF column (GE Healthcare) using a linear NaCl gradient up to 1 M NaCl. Fractions containing the GFP lunasin fusion were identified by examination under UV illumination and by immunoblot analysis of SDS PAGE gels using a lunasin-specific monoclonal antibody. Fractions containing the GFP-lunasin fusion were pooled and used for these studies.

With continued reference to FIG. 2, Coomassie-stained SDS-PAGE gel (FIG. 2A) and corresponding immunoblot of a duplicate gel probed with a lunasin-specific antibody (FIG. 2B) are shown. Samples included on the gel and immunoblot are: M, SeeBlue Plus2 protein markers (Invitrogen); 1, anion-exchange purified GFP-lunasin fractions; 2, anion-exchange purified GFP-lunasin fractions treated with 5 units of purified thrombin; 3, 5 units of purified thrombin alone; 300 ng of synthetic lunasin peptide. * Indicates the protein band corresponding the GFP-lunasin fusion. ** Indicates the protein band corresponding to the lunasin peptide released by thrombin cleavage.

Figure 3:
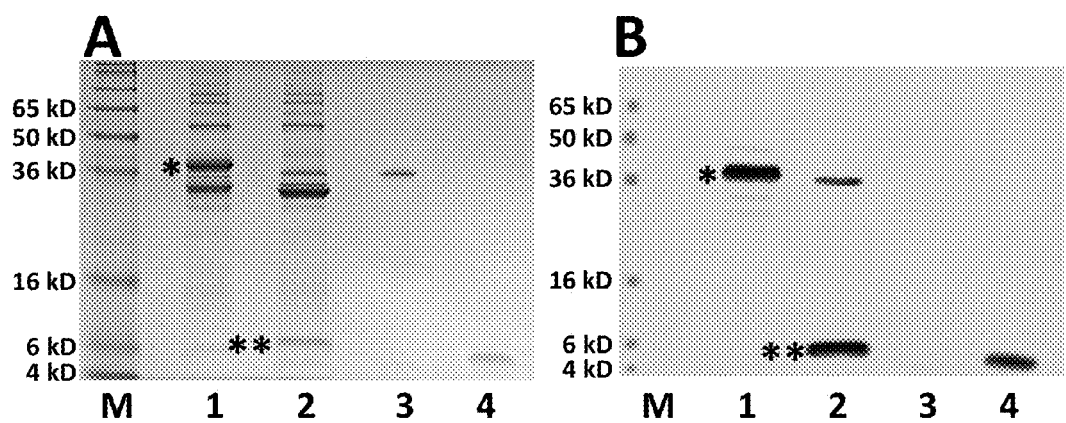
FIG. 3A is a Commassie-stained gel showing that the GFP-RGD-lunasin fusion protein was expressed in *Nicotiana benthamiana* plants and that RGD-lunasin can be released from the fusion protein by protease cleaveage.
FIG. 3B is a corresponding immunoblot probed with an antibody against lunasin confirming that the GFP-RGD-lunasin fusion protein was expressed in *Nicotiana benthamiana* plants and that RGD-lunasin can be released from the fusion protein by protease cleaveage.

FIG. 3 includes an analysis of partially purified GFP-RGD-lunasin fusion protein expressed in tobacco plants and the successful release of lunasin from the fusion protein by thrombin cleavage. An expression construct was generated using a Geneware® vector such that RGD-lunasin is translationally fused to the C-terminal end of GFP using a peptide linker containing a cleavage site for the protease, thrombin (See SEQ ID NO: 3). Infectious transcripts were generated from the Geneware® construct and inoculated into *Nicotiana benthamiana* plants. Infected plants were harvested 5-10 days after inoculation and tissues extracted with phosphate buffered saline (58.5 mM Na2HPO4, 17 mM NaH2PO$_4$, 68.4 mM NaCl, 20 mM ascorbic acid, 10 mM sodium metabisulfite). Crude extracts were filtered through 4 layers of cheesecloth and 1 layer of miracloth. The filtrate was then centrifuged at 10,000×G for 10 minutes to generate a clarified extract. The clarified extract is subjected to anion-exchange chromatography on a Q Sepharose FF column (GE Healthcare) using a linear NaCl gradient up to 1 M NaCl. Fractions containing the GFP lunasin fusion were identified by examination under UV illumination and by immunoblot analysis of SDS PAGE gels using a lunasin-specific monoclonal antibody. Fractions containing the GFP-lunasin fusion were pooled and used for these studies.

With continued reference to FIG. 3, Coomassie-stained SDS-PAGE gel (FIG. 3A) and corresponding immunoblot of a duplicate gel probed with a lunasin-specific antibody (FIG. 3B) are shown. Samples included on the gel and immunoblot are: M, SeeBlue Plus2 protein markers (Invitrogen); 1, anion-exchange purified GFP-RGD-lunasin fractions; 2, anion-exchange purified GFP-RGD-lunasin fractions treated with 5 units of purified thrombin; 3, 5 units of purified thrombin alone; 300 ng of synthetic lunasin peptide. * Indicates the protein band corresponding the GFP-RGD-lunasin fusion. ** Indicates the protein band corresponding to the lunasin peptide released by thrombin cleavage.

The results of the studies described herein indicate that the use of a plant-based expression system was successful and the expression levels are sufficient for larger-scale production.

Throughout this document, various references are mentioned. All such references are incorporated herein by reference, including the references set forth in the following list:

REFERENCES

1. Ampe, C., VanDamme, J., deCastro, L. A. B., Sampaio, M. J. A. M., VanMontagu, M., Vandekerckhove, J. (1986) The amino-acid sequence of the 2S sulphur-rich proteins from seeds of Brazil numt (*Bertholletia excelsa* H.B.K.). Eur. J. Biochem. 159, 597-604.
2. de Lumen, B. O. (2008). Lunasin: a novel cancer preventive seed peptide that modifies chromatin. J AOAC Int 91, 932-935.
3. Ericson, M. L., Rodin, J., Lenman, M., Glimelius, K., Josefsson, L-G., Rask, L. (1986) Structure of the Rapeseed 1.7 S Storage Protein, Napin, and its Precursor. J. Biological Chem. 261, 14576-14581.
4. Galvez, A. F., and de Lumen, B. O. (1999). A soybean cDNA encoding a chromatin-binding peptide inhibits mitosis of mammalian cells. Nat Biotechnol 17, 495-500.
5. Hernandez-Ledesma, B., Hsieh, C. C., and de Lumen, B. O. (2009). Lunasin, a novel seed peptide for cancer prevention. Peptides 30, 426-430.
6. Li, S., McGuire, M. J., Lin, M., Liu, Y-H., Oyama, T., Sun, X., and Brown, K. C. (2009). Synthesis and characterization of a high-affinitiy $α_vβ_6$-specific ligand for in vitro and in vivo applications. Mol. Cancer. Ther. 8(5), 1239-48.
7. Lin, J., Fido, R., Shewry, P., Archer, D. B., Alcocer, M. J. C. (2004) The expression and processing of two recombinant 2S albumins from soybean (*Glycine max*) in the yeast *Pichia pastoris*. Biochimica et Biophysica Acta 1698, 203-212.
8. Liu, C.-F., Pan, T.-M. (2010) Recominant expression of bioactive peptide lunasin in *Escherichia coli*. Appl. Microbiol. Biotechnol.
9. Chiesa, G., Rigamonti, E., Lovati, M. R., Disconzi, E., Soldati, S., Sacco, M. G., Cato, E. M., Patton, V., Scanziani, E., Vezzoni, P., Arnoldi, A., Locati, D., and Sirtori, C. R. (2008). Reduced mammary tumor progression in a transgenic mouse model fed an isoflavone-poor soy protein concentrate. Mol Nutr Food Res.
10. de Lumen, B. O. (2005). Lunasin: a cancer-preventive soy peptide. Nutr Rev 63, 16-21.
11. de Lumen, B. O. (2008). Lunasin: a novel cancer preventive seed peptide that modifies chromatin. J AOAC Int 91, 932-935.
12. de Mejia, E. G., Bradford, T., and Hasler, C. (2003). The anticarcinogenic potential of soybean lectin and lunasin. Nutr Rev 61, 239-246.
13. de Mejia, E. G., and Dia, V. P. (2009). Lunasin and lunasin-like peptides inhibit inflammation through suppression of NF-kappaB pathway in the macrophage. Peptides 30, 2388-2398.
14. de Mejia, E. G., Wang, W., and Dia, V. P. (2010). Lunasin, with an arginine-glycine-aspartic acid motif, causes apoptosis to L1210 leukemia cells by activation of caspase-3. Mol Nutr Food Res 54, 406-414.
15. Dia, V. P., Berhow, M. A., and Gonzalez De Mejia, E. (2008). Bowman-Birk inhibitor and genistein among soy compounds that synergistically inhibit nitric oxide and prostaglandin E2 pathways in lipopolysaccharide-induced macrophages. J Agric Food Chem 56, 11707-11717.

16. Dia, V. P., Wang, W., Oh, V. L., de Lumen, B. O., and de Mejia, E. G. (2009). Isolation, purification and characterization of lunasin from defatted soybean flour and in vitro evaluation of its anti-inflammatory activity. Food Chemistry 114, 108-115.
17. Dia, V. P., Torres, S., De Lumen, B. O., Erdman, J. W., Jr., and De Mejia, E. G. (2009). Presence of lunasin in plasma of men after soy protein consumption. J Agric Food Chem 57, 1260-1266.
18. Dia, V. P., and Mejia, E. G. (2010). Lunasin promotes apoptosis in human colon cancer cells by mitochondrial pathway activation and induction of nuclear clusterin expression. Cancer Lett 295, 44-53.
19. Galvez, A. F., Chen, N., Macasieb, J., and de Lumen, B. O. (2001). Chemopreventive property of a soybean peptide (lunasin) that binds to deacetylated histones and inhibits acetylation. Cancer Res 61, 7473-7478.
20. Galvez, A. F., and de Lumen, B. O. (1999). A soybean cDNA encoding a chromatin-binding peptide inhibits mitosis of mammalian cells. Nat Biotechnol 17, 495-500.
21. Gonzalez de Mejia, E., Vasconez, M., de Lumen, B. O., and Nelson, R. (2004). Lunasin concentration in different soybean genotypes, commercial soy protein, and isoflavone products. J Agric Food Chem 52, 5882-5887.
22. Hernandez-Ledesma, B., Hsieh, C. C., and de Lumen, B. O. (2009). Lunasin, a novel seed peptide for cancer prevention. Peptides 30, 426-430.
23. Hsieh, E. A., Chai, C. M., de Lumen, B. O., Neese, R. A., and Hellerstein, M. K. (2004). Dynamics of keratinocytes in vivo using HO labeling: a sensitive marker of epidermal proliferation state. J Invest Dermatol 123, 530-536.
24. Hsieh, C. C., Hernandez-Ledesma, B., and de Lumen, B. O. (2010a). Lunasin, a novel seed peptide, sensitizes human breast cancer MDA-MB-231 cells to aspirin-arrested cell cycle and induced apoptosis. Chem Biol Interact 186, 127-134.
25. Hsieh, C. C., Hernandez-Ledesma, B., Jeong, H. J., Park, J. H., and de Lumen, B. O. (2010b). Complementary roles in cancer prevention: protease inhibitor makes the cancer preventive peptide lunasin bioavailable. PLoS One 5, e8890.
26. Jeong, H. J., Lam, Y., and de Lumen, B. O. (2002). Barley lunasin suppresses ras-induced colony formation and inhibits core histone acetylation in mammalian cells. J Agric Food Chem 50, 5903-5908.
27. Jeong, H. J., Park, J. H., Lam, Y., and de Lumen, B. O. (2003). Characterization of lunasin isolated from soybean. J Agric Food Chem 51, 7901-7906.
28. Jeong, H. J., Jeong, J. B., Kim, D. S., and de Lumen, B. O. (2007a). Inhibition of core histone acetylation by the cancer preventive peptide lunasin. J Agric Food Chem 55, 632-637.
29. Jeong, H. J., Jeong, J. B., Kim, D. S., Park, J. H., Lee, J. B., Kweon, D. H., Chung, G. Y., Seo, E. W., and de Lumen, B. O. (2007b). The cancer preventive peptide lunasin from wheat inhibits core histone acetylation. Cancer Lett 255, 42-48.
30. Jeong, J. B., Jeong, H. J., Park, J. H., Lee, S. H., Lee, J. R., Lee, H. K., Chung, G. Y., Choi, J. D., and de Lumen, B. O. (2007c). Cancer-preventive peptide lunasin from *Solanum nigrum* L. inhibits acetylation of core histones H3 and H4 and phosphorylation of retinoblastoma protein (Rb). J Agric Food Chem 55, 10707-10713.
31. Jeong, H. J., Lee, J. R., Jeong, J. B., Park, J. H., Cheong, Y. K., and de Lumen, B. O. (2009). The cancer preventive seed peptide lunasin from rye is bioavailable and bioactive. Nutr Cancer 61, 680-686.
32. Krebbers, E., Herdies, L., DeClercq, A., Seurinck, J., Leemans, J., VanDamme, J., Segura, M., Gheysen, G., VanMontagu, M., and Vandekerckhove, J. (1988) Determination of the Processing Sites of an *Arabidopisis* 2S Albumin and Characterization of the Complete Gene Family. Plant Physiol, 81, 859-866.
33. Lam, Y., Galvez, A., and de Lumen, B. O. (2003). Lunasin suppresses E1A-mediated transformation of mammalian cells but does not inhibit growth of immortalized and established cancer cell lines. Nutr Cancer 47, 88-94.
34. Liu, C. F., and Pan, T. M. (2010). Recombinant expression of bioactive peptide lunasin in *Escherichia coli*. Appl Microbiol Biotechnol. 88, 177-186.
35. Maldonado-Cervantes, E., Jeong, H. J., Leon-Galvan, F., Barrera-Pacheco, A., DeLeon-Rodriguez, A., de Mejia, E. G., deLumen, B. O., de la Rosa, A. P. B. (2010). Amaranth lunasin-like peptide internalizes into the cell nucleus and inhibits chemical carcinogen-induced transformation of NIH-3T3 cells. Peptides.
36. Martin, G. A., Kawaguchi, R., Lam, Y., DeGiovanni, A., Fukushima, M., and Mutter, W. (2001). High-yield, in vitro protein expression using a continuous-exchange, coupled transcription/translation system. Biotechniques 31, 948-950, 952-943.
37. Odani, S., Koide, T., & Ono, T. (1987). Amino Acid Sequence of a Soybean (*Glycine max*) Seed Polypeptide Having a Poly(L-Aspartic Acid) Structure. The Journal of Biological Chemistry 262, 10502-10505.
38. Park, J. H., Jeong, H. J., and de Lumen, B. O. (2005). Contents and bioactivities of lunasin, bowman-birk inhibitor, and isoflavones in soybean seed. J Agric Food Chem 53, 7686-7690.
39. Park, J. H., Jeong, H. J., and Lumen, B. O. (2007). In vitro digestibility of the cancer-preventive soy peptides lunasin and BBI. J Agric Food Chem 55, 10703-10706.
40. Silva-Sanchez, C., de la Rosa, A. P., Leon-Galvan, M. F., de Lumen, B. O., de Leon-Rodriguez, A., and de Mejia, E. G. (2008). Bioactive peptides in amaranth (*Amaranthus hypochondriacus*) seed. J Agric Food Chem 56, 1233-1240.
41. Wang, W., Bringe, N. A., Berhow, M. A., and Gonzalez de Mejia, E. (2008a). beta-Conglycinins among sources of bioactives in hydrolysates of different soybean varieties that inhibit leukemia cells in vitro. J Agric Food Chem 56, 4012-4020.
42. Wang, W., Dia, V. P., Vasconez, M., de Mejia, E. G., and Nelson, R. L. (2008b). Analysis of soybean protein-derived peptides and the effect of cultivar, environmental conditions, and processing on lunasin concentration in soybean and soy products. J AOAC Int 91, 936-946.
43. U.S. Pat. No. 7,404,973 Bowman-Birk inhibitor soy protein concentrate composition
44. U.S. Pat. No. 7,375,092 Lunasin peptides
45. U.S. Pat. No. 7,309,688 Topical anti-cancer compositions and methods of use thereof
46. U.S. Pat. No. 7,192,615 Compositions containing legume products
47. U.S. Pat. No. 6,544,956 Lunasin peptides
48. U.S. Pat. No. 6,391,848 Soybean protein nutraceuticals
49. U.S. Pat. No. 6,107,287 Lunasin peptides
50. International Patent Application Publication No. WO/2001/034808 to Peters for "Method of Large-Scale Production and Method of Testing of the Biological Activity of a Substance from Soybean."
51. U.S. Patent Application Publication No. 2010/0197594 METHODS FOR USING SOY PEPTIDES TO INHIBIT H3 ACETYLATION, REDUCE EXPRESSION OF HMG-COA REDUCTASE AND INCREASE LDL RECEPTOR AND SP1 EXPRESSION IN A MAMMAL
52. U.S. Patent Application Publication No. 2008/0070827 METHODS FOR USING SOY PEPTIDES TO INHIBIT H3 ACETYLATION, REDUCE EXPRESSION OF HMG COA REDUCTASE, AND INCREASE LDL RECEPTOR AND SP1 EXPRESSION IN A MAMMAL
53. U.S. Patent Application Publication No. 2008/0003567 Use of Lunasin Peptide as a Transcriptional Activator to Prevent Cancer and Related Methods for Treatment, Monitoring and Prognosis
54. U.S. Patent Application Publication No. 2007/0292494 Carbohydrate-Derivatized Liposomes for Targeting Cellular Carbohydrate Recognition Domains of Ctl/Ctld Lectins, and Intracellular Delivery of Therapeutically Active Compounds
55. U.S. Patent Application Publication No. 2007/0054031 Methods of extracting, concentrating and fractionating proteins and other chemical components
56. U.S. Patent Application Publication No. 2003/0229038 Lunasin peptides
57. U.S. Patent Application Publication No. 2003/0224420 Method for obtaining and measuring proliferation of long-term label retaining cells and stem cells
58. U.S. Patent Application Publication No. 2003/0064121 High protein, Bowman-Birk Inhibitor Concentrate and process for its manufacture
59. U.S. Patent Application Publication No. 2003/0027765 Therapeutic peptides having a motif that binds specifically to non-acetylated H3 and H4 histones for cancer therapy It will be understood that various details of the presently disclosed subject matter can be changed without departing from the scope of the subject matter disclosed herein. Furthermore, the foregoing description is for the purpose of illustration only, and not for the purpose of limitation.

---

What is claimed is:

1. A method of producing a lunasin polypeptide in a plant, said method comprising:
    introducing an expression vector comprising a polynucleotide encoding a fusion protein into a plant cell, said fusion protein comprising
        the lunasin polypeptide;
        a green fluorescent protein; and
        a site-specific protease cleavage site; and
    expressing the fusion protein within the plant, wherein said fusion protein is not toxic to the plant cell.

2. The method of claim 1, wherein the expression vector is a transient expression vector and the plant cell is a non-dividing plant cell.

3. The method of claim 1, wherein the expression vector is a tobacco mosaic virus (TMV)-based DNA plasmid.

4. The method of claim 1, wherein the plant cell is a *Nicotiana benthamiana* cell.

5. The method of claim 1 further comprising isolating the fusion protein.

6. The method of claim 5 further comprising cleaving the lunasin polypeptide from the fusion protein.

7. The method of claim 5, and further comprising cleaving a lunasin polypeptide-containing fusion protein from the remainder of the fusion protein expressed within the plant.

8. The method of claim 7, wherein the lunasin polypeptide-containing fusion protein further comprises a polypeptide targeting signal for directing the lunasin polypeptide to a target cell.

9. The method of claim 1, wherein the lunasin polypeptide is produced in amounts of about >100 mg/kg fresh weight plant tissue.

10. A method of producing a lunasin polypeptide in a plant, said method comprising:
    providing an expression vector comprising a polynucleotide encoding a fusion protein including:
        the lunasin polypeptide;
        a green fluorescent protein; and
        a site-specific protease cleavage site;
    introducing the expression vector into a plant cell;
    isolating the fusion protein; and
    using a protease of the site-specific protease cleavage site to obtain the lunasin polypeptide or a desired lunasin polypeptide-containing fusion protein, wherein said fusion protein is not toxic to the plant cell.

11. The method of claim 10, wherein the lunasin polypeptide is produced in amounts of about >100 mg/kg fresh weight plant tissue.

12. The method of claim 10, wherein the desired lunasin polypeptide-containing fusion protein further comprises a polypeptide targeting signal for directing the lunasin polypeptide to a target cell.

13. The method of claim 10, wherein the expression vector is a transient expression vector and the plant cell is a non-dividing plant cell.

14. The method of claim 10, wherein the expression vector is a tobacco mosaic virus (TMV)-based DNA plasmid.

15. The method of claim 10, wherein the plant cell is a *Nicotiana benthamiana* cell.

* * * * *

SEQUENCE LISTING

```
<160> NUMBER OF SEQ ID NOS: 4

<210> SEQ ID NO 1
<211> LENGTH: 44
<212> TYPE: PRT
<213> ORGANISM: Glycine max

<400> SEQUENCE: 1

Met Ser Lys Trp Gln His Gln Gln Asp Ser Cys Arg Lys Gln Leu Gln
1               5                   10                  15

Gly Val Asn Leu Thr Pro Cys Glu Lys His Ile Met Glu Lys Ile Gln
            20                  25                  30

Gly Arg Gly Asp Asp Asp Asp Asp Asp Asp
        35                  40

<210> SEQ ID NO 2
<211> LENGTH: 54
<212> TYPE: PRT
<213> ORGANISM: Artificial Sequence
<220> FEATURE:
<223> OTHER INFORMATION: Fusion Protein

<400> SEQUENCE: 2

Met Arg Gly Asp Leu Ala Thr Leu Arg Gln Leu Ser Lys Trp Gln His
1               5                   10                  15

Gln Gln Asp Ser Cys Arg Lys Gln Leu Gln Gly Val Asn Leu Thr Pro
            20                  25                  30

Cys Glu Lys His Ile Met Glu Lys Ile Gln Gly Arg Gly Asp Asp Asp
        35                  40                  45

Asp Asp Asp Asp Asp Asp
    50

<210> SEQ ID NO 3
<211> LENGTH: 71
<212> TYPE: PRT
<213> ORGANISM: artificial sequence
<220> FEATURE:
<223> OTHER INFORMATION: Fusion Protein

<400> SEQUENCE: 3

Gly Gly Gly Ser Gly Gly Gly Ser Gly Gly Gly Ser Leu Val Pro Arg
1               5                   10                  15
```

-continued

```
Gly Ser Arg Gly Asp Leu Ala Thr Leu Arg Gln Leu Ser Lys Trp Gln
             20                  25                  30

His Gln Gln Asp Ser Cys Arg Lys Gln Leu Gln Gly Val Asn Leu Thr
         35                  40                  45

Pro Cys Glu Lys His Ile Met Glu Lys Ile Gln Gly Arg Gly Asp Asp
     50                  55                  60

Asp Asp Asp Asp Asp Asp Asp
65                  70

<210> SEQ ID NO 4
<211> LENGTH: 60
<212> TYPE: PRT
<213> ORGANISM: Artificial Sequence
<220> FEATURE:
<223> OTHER INFORMATION: Fusion Protein

<400> SEQUENCE: 4

Gly Gly Gly Ser Gly Gly Gly Ser Gly Gly Gly Ser Leu Val Pro Arg
1               5                   10                  15

Gly Ser Lys Trp Gln His Gln Gln Asp Ser Cys Arg Lys Gln Leu Gln
             20                  25                  30

Gly Val Asn Leu Thr Pro Cys Glu Lys His Ile Met Glu Lys Ile Gln
         35                  40                  45

Gly Arg Gly Asp Asp Asp Asp Asp Asp Asp Asp
     50                  55                  60
```